(12) United States Patent
Nitta et al.

(10) Patent No.: US 9,098,927 B2
(45) Date of Patent: Aug. 4, 2015

(54) IMAGE PROCESSING APPARATUS FOR DIAGNOSTIC IMAGING AND METHOD THEREOF

(75) Inventors: Shuhei Nitta, Tokyo (JP); Tomoyuki Takeguchi, Kanagawa (JP); Masahide Nishiura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 461 days.

(21) Appl. No.: 13/389,334

(22) PCT Filed: Aug. 21, 2009

(86) PCT No.: PCT/JP2009/004029
§ 371 (c)(1),
(2), (4) Date: Feb. 7, 2012

(87) PCT Pub. No.: WO2011/021254
PCT Pub. Date: Feb. 24, 2011

(65) Prior Publication Data
US 2012/0134566 A1    May 31, 2012

(51) Int. Cl.
*G06K 9/00* (2006.01)
*G06T 19/00* (2011.01)
(Continued)

(52) U.S. Cl.
CPC ............... *G06T 19/00* (2013.01); *A61B 6/5223* (2013.01); *A61B 8/523* (2013.01); *A61B 5/055* (2013.01); *A61B 6/03* (2013.01); *G06T 2219/008* (2013.01); *G06T 2219/028* (2013.01)

(58) Field of Classification Search
None
See application file for complete search history.

(56) References Cited

U.S. PATENT DOCUMENTS 5,107,838 A    4/1992  Yamaguch
5,469,254 A *  11/1995 Konomura ................. 356/241.1
(Continued)

FOREIGN PATENT DOCUMENTS

JP    01-134580    5/1989
JP    04-218139    8/1992
(Continued)

OTHER PUBLICATIONS

Japanese Office Action for Japanese Application No. 2011-527494 mailed on Nov. 13, 2012.
(Continued)

*Primary Examiner* — Chan Park
*Assistant Examiner* — Iman K Kholdebarin
(74) *Attorney, Agent, or Firm* — Oblon, McClelland, Maier & Neustadt, L.L.P.

(57) ABSTRACT

An image processing apparatus for diagnostic imaging, which allows easy verification of a spatial position on an arbitrary cross section is provided. An image processing apparatus 1 includes a basic position calculating unit 2 configured to calculate a position of a basic cross section from an image data, an auxiliary position calculating unit 3 configured to calculate a position of an auxiliary cross section, a generating unit 4 configured to generate a basic cross-sectional image using the image data and the position of the basic cross section and generate an auxiliary cross-sectional image using the image data and the position of the auxiliary cross section, a relationship calculating unit 5 configured to calculate information on a positional relationship indicating the relative positional relationship between the position of the basic cross section and the position of the auxiliary cross section, and a combining unit 6 configured to combine the information on the positional relationship with the basic cross-sectional image or the auxiliary cross-sectional image respectively, and a display unit 9 configured to display the combined image.

13 Claims, 8 Drawing Sheets

(b)

(51) Int. Cl.
*A61B 6/00* (2006.01)
*A61B 8/08* (2006.01)
A61B 5/055 (2006.01)
A61B 6/03 (2006.01)

(56) References Cited

U.S. PATENT DOCUMENTS

| | | | |
|---|---|---|---|
| 5,971,767 A * | 10/1999 | Kaufman et al. | 434/267 |
| 6,381,296 B1 * | 4/2002 | Nishiura | 378/4 |
| 8,340,374 B2 * | 12/2012 | Yamagata | 382/128 |
| 8,480,582 B2 * | 7/2013 | Tsujino et al. | 600/437 |
| 2004/0249270 A1 | 12/2004 | Kondo et al. | |
| 2005/0033160 A1 * | 2/2005 | Yamagata et al. | 600/425 |
| 2006/0056730 A1 * | 3/2006 | Matsumoto | 382/285 |
| 2006/0290695 A1 * | 12/2006 | Salomie | 345/420 |
| 2006/0291717 A1 * | 12/2006 | Mussack et al. | 382/154 |
| 2007/0141526 A1 * | 6/2007 | Eisenberg et al. | 433/24 |
| 2008/0137926 A1 * | 6/2008 | Skinner et al. | 382/131 |
| 2008/0186378 A1 * | 8/2008 | Shen et al. | 348/65 |
| 2008/0240494 A1 * | 10/2008 | Oosawa et al. | 382/100 |
| 2008/0292155 A1 * | 11/2008 | Goto et al. | 382/128 |
| 2009/0018448 A1 * | 1/2009 | Seo et al. | 600/443 |
| 2009/0060306 A1 * | 3/2009 | Ohuchi et al. | 382/131 |
| 2009/0257630 A1 * | 10/2009 | Liang et al. | 382/128 |
| 2010/0069756 A1 * | 3/2010 | Ogasawara et al. | 600/447 |
| 2010/0121189 A1 * | 5/2010 | Ma et al. | 600/437 |
| 2010/0249593 A1 * | 9/2010 | Takeguchi et al. | 600/443 |
| 2012/0134566 A1 * | 5/2012 | Nitta et al. | 382/131 |
| 2012/0237105 A1 * | 9/2012 | Mielekamp | 382/132 |
| 2014/0133726 A1 * | 5/2014 | Garner et al. | 382/131 |

FOREIGN PATENT DOCUMENTS

| | | | | |
|---|---|---|---|---|
| JP | 2003-325514 | | 11/2003 | |
| JP | 2005-087237 | | 4/2005 | |
| JP | 2005087237 A | * | 4/2005 | A61B 8/06 |
| JP | 2005095279 A | * | 4/2005 | A61B 8/06 |

OTHER PUBLICATIONS

International Search Report for International Application No. PCT/JP2009/004029 mailed on Sep. 29, 2009.
Japanese Second Office Action of Notification of Reasons for Refusal for Application No. 2011-527494 Dated Feb. 19, 2013, 5 pgs.

* cited by examiner (a)

(b)

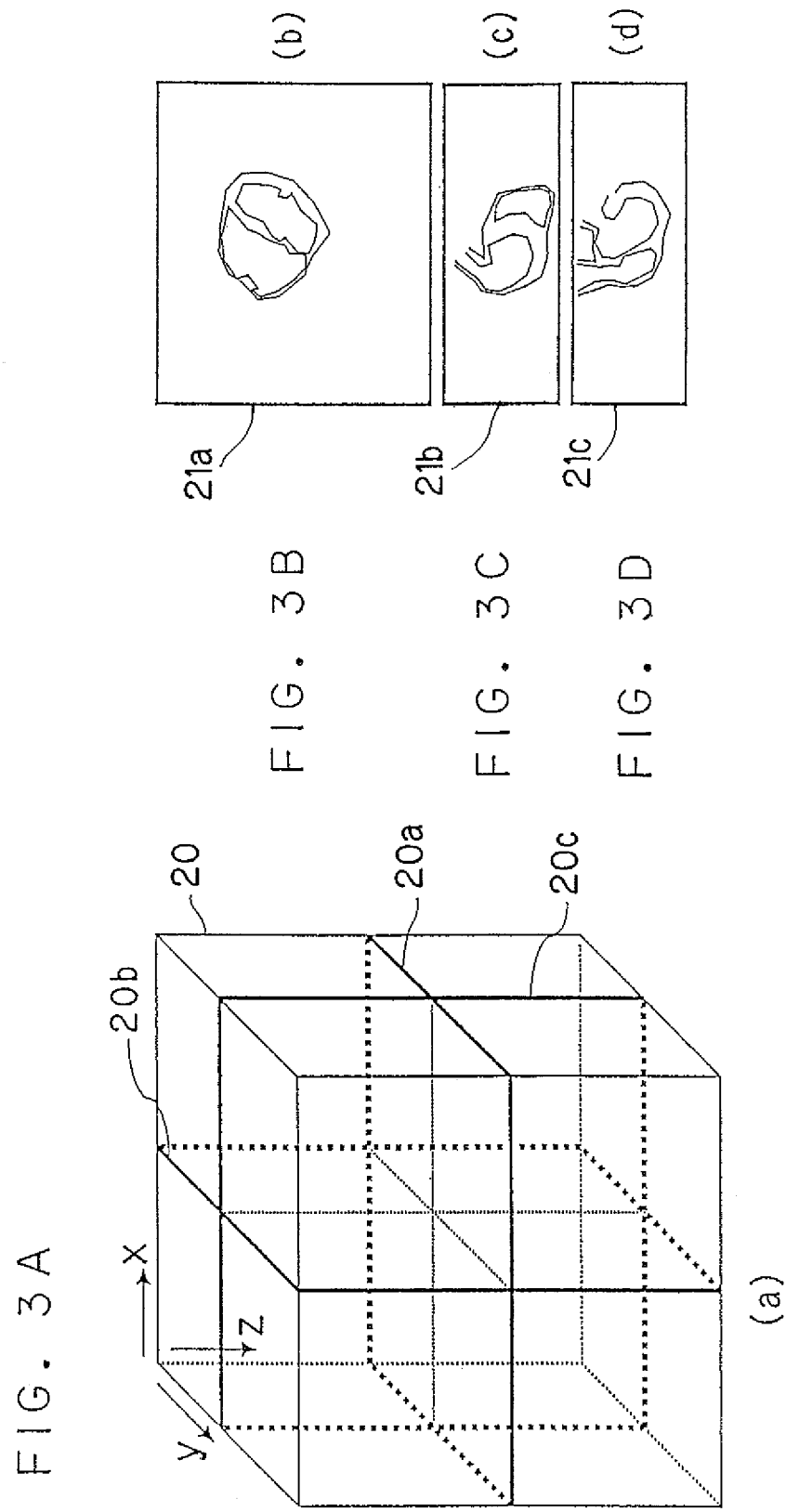

(a)

(b)

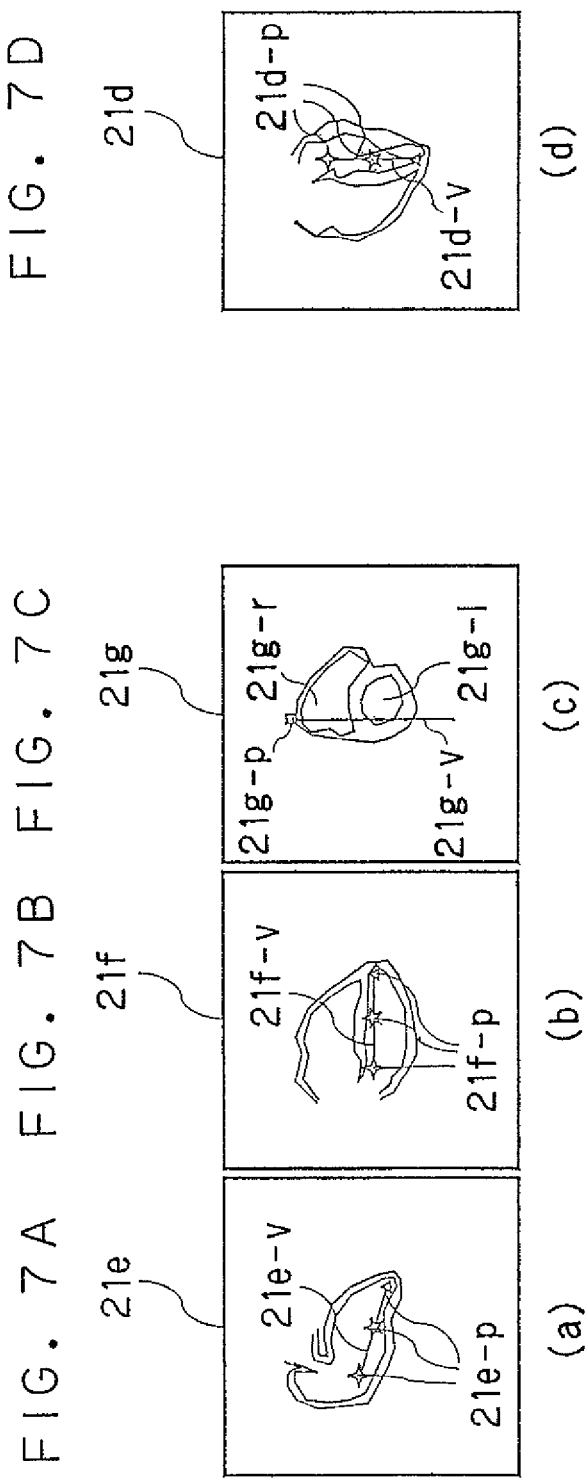

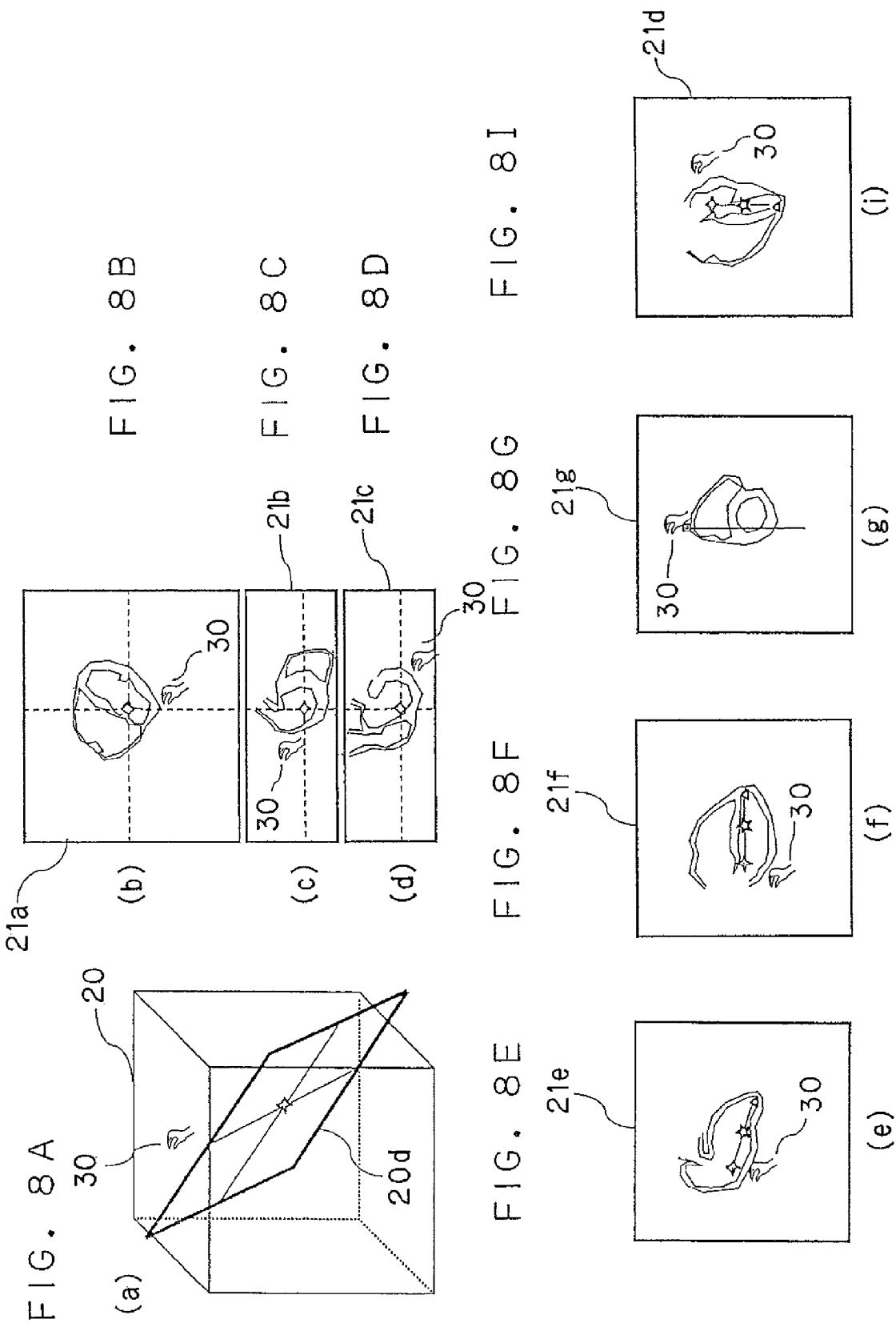

IMAGE PROCESSING APPARATUS FOR DIAGNOSTIC IMAGING AND METHOD THEREOF

TECHNICAL FIELD

The present invention relates to a medical-use image processing technique for displaying an arbitrary cross section from a three-dimensional medical-use image data.

BACKGROUND ART

Patent Document 1 sets plural arbitrary positions of cross sections from a three-dimensional medical-use image data shot via X-ray CT or MRI. Then, Patent Document 1 sets an arbitrary cross section for a portion to be diagnosed when diagnosing on the portion-by-portion basis from the medical-use image data.

Patent Document 1: JP-A-4018303

DISCLOSURE OF INVENTION

Problems to be Solved by the Invention

However, in Patent Document 1, since only the intended cross section and a rough position in the three-dimensional space of the cross-sectional image are referenced, there is a problem in that satisfactory verification of the spatial position of the cross section cannot be achieved.

In order to solve the problem described above, it is an object of the present invention to provide a medical-use image processing apparatus which allows easy verification of the spatial position of an arbitrary cross section and a method thereof.

Means for Solving the Problems

The present invention provides an image processing apparatus for diagnostic imaging, including: a basic position calculating unit configured to calculate a position of a basic cross section indicating a spatial position of the basic cross section in a three-dimensional image space from a three-dimensional image data including an arbitrary portion; an auxiliary position calculating unit configured to calculate at least one position of an auxiliary cross section indicating a spatial position of the auxiliary cross section as a cross section intersecting the basic cross section; a generating unit configured to generate a basic cross-sectional image using the image data and the position of the basic cross section and generate an auxiliary cross-sectional image using the image data and the position of the auxiliary cross section; a relationship calculating unit configured to calculate information on a positional relationship indicating the relative positional relationship between the position of the basic cross section and the position of the auxiliary cross section; a combining unit configured to combine the information of the positional relationship with the basic cross-sectional image or the auxiliary cross-sectional image respectively; and a display unit configured to display the combined image.

Advantages of the Invention

According to the present invention, easy verification of the spatial position of a basic cross section is achieved.

BRIEF DESCRIPTION OF THE DRAWINGS

FIG. 3(a) is an explanatory drawing showing an Axial cross section, a Sagittal cross section, and a Coronal cross section of a three-dimensional image space 20, and (b) to (d) are an Axial cross-sectional image, a Sagittal cross-sectional image, and a Coronal cross-sectional image.

FIGS. 7(a) to (c) are drawings of the auxiliary cross-sectional image, and (d) is a drawing of a basic cross-sectional image.

FIG. 8(a) is an explanatory drawing showing the basic cross section of the three-dimensional image space 20, (b) to (g) are drawings of the auxiliary cross-sectional image, and (i) is a drawing showing the basic cross-sectional image.

REFERENCE NUMERALS

1 . . . image processing apparatus for diagnostic imaging, 2 . . . basic position calculating unit, 3 . . . auxiliary position calculating unit, 4 . . . generating unit, 5 . . . relationship calculating unit, 6 . . . a combining unit, 7 . . . input unit, 8 . . . correcting unit, 9 . . . display unit

Best Modes For Carrying Out The Invention

Referring now to FIG. 1 to FIG. 8, an image processing apparatus 1 according to an embodiment of the present invention will be described.

The present embodiment is effective for a diagnostic imaging apparatus such as X-ray CT, MRI, ultrasonic wave or the like and, specifically, is suitable for a case where a cross-sectional image at an arbitrary spatial position for a portion to be diagnosed is required.

In the present embodiment, an internal organ to be diagnosed is a heart, and a "four-chamber cross-sectional image" is described as a detailed example of a basic cross section. The term "basic cross section" is a cross section set to include an arbitrary portion used by a doctor for diagnosis. The basic cross section is not limited to the four-chamber cross-sectional image, and may be, for example, a "two-chamber cross-sectional image" or a "left-chamber short axis view".

Figure 1:
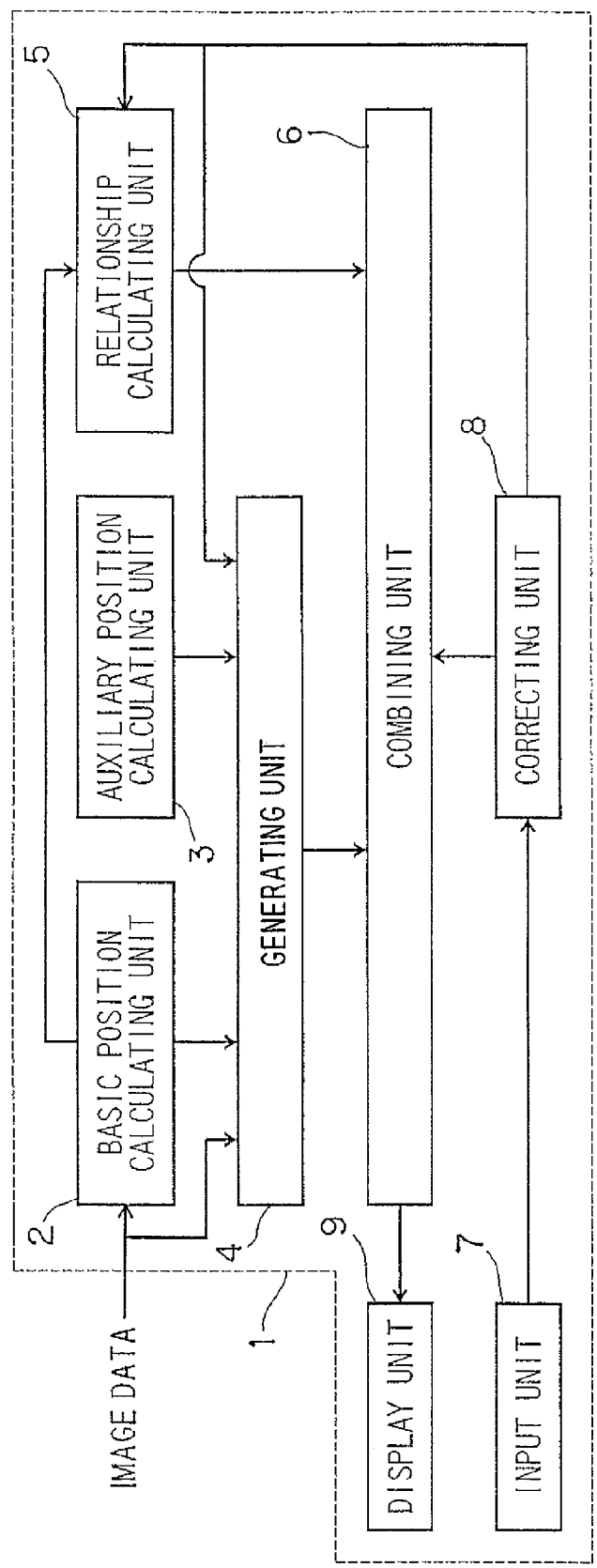
FIG. 1 is a block diagram showing an image processing apparatus for diagnostic imaging according to an embodiment.

Referring now to FIG. 1, a configuration of the image processing apparatus 1 will be described. FIG. 1 is a block diagram showing a configuration of the image processing apparatus 1.

As shown in FIG. 1, the image processing apparatus 1 includes a basic position calculating unit 2, an auxiliary position calculating unit 3, a generating unit 4, a relationship calculating unit 5, a combining unit 6, an input unit 7, a correcting unit 8, and a display unit 9.

Image data(medical-use image data) as a three-dimensional volume data obtained from a diagnostic imaging apparatus such as X-ray CT, MRI, or ultrasonic waves is entered into the basic position calculating unit 2 and the generating unit 4.

The basic position calculating unit 2 calculates a position of a basic cross section showing a spatial position of the basic cross section from the image data.

The auxiliary position calculating unit 3 calculates a position of an auxiliary cross section showing a spatial position of the auxiliary cross section intersecting the basic cross section from the position of the basic cross section.

The generating unit 4 generates a basic cross-sectional image using the position of the basic cross section and the image data, and generates an auxiliary cross sectional image using the position of the auxiliary cross section and the image data.

The relationship calculating unit 5 calculates information on relative positional relationship between the position of the basic cross section and the position of the auxiliary cross section with respect to each other.

The combining unit 6 combines the information on relative positional relationship of the respective cross sections calculated by the relationship calculating unit 5 with the basic cross sectional image and the auxiliary cross-sectional image, and displays the same on the display unit 9. The display unit 9 is a display of a liquid crystal display apparatus, a CRT, or the like.

The input unit 7 is means for entering correction information relating to the information on positional relationship of the basic cross-sectional image and the auxiliary cross-sectional image. For example, the input unit 7 is realized by a user interface such as a mouse, a keyboard, a track ball, or a touch pad.

The correcting unit 8 corrects the position of the basic cross section and the position of the auxiliary cross section on the basis of the correction information received by the input unit 7.

The relationship between the four-chamber cross-sectional image and a characteristic portion of a heart will be described with reference to FIG. 2.

Figure 2A:
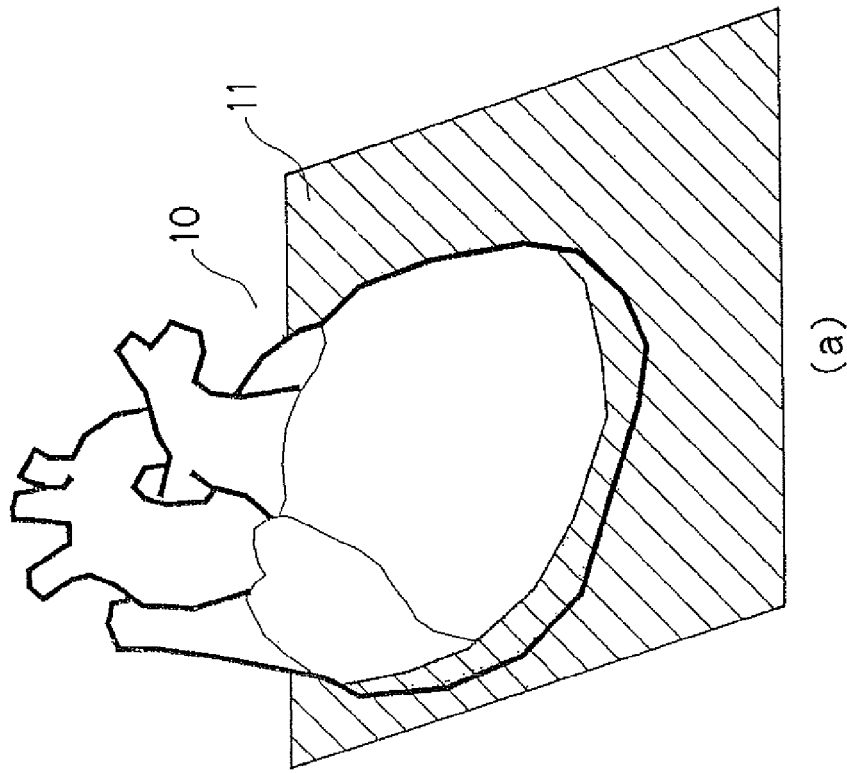
FIGS. 2(a) and 2(b) are explanatory drawings showing an anatomical situation of a four-chamber cross-sectional image.
Figure 2B:
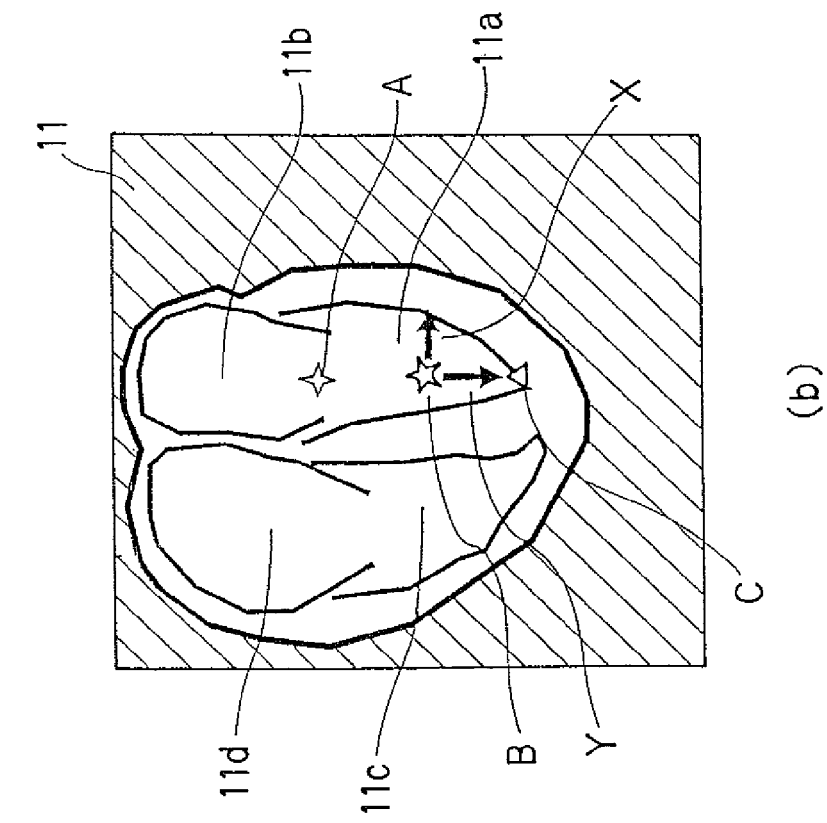

FIG. 2(a) shows an anatomical situation 10 of a four-chamber cross-sectional image, and FIG. 2(b) shows an example of a four-chamber cross-sectional image 11. As shown in FIG. 2(b), the four-chamber cross-sectional image includes all the four chambers of a heart (a left ventricle 11a, a left atrium 11b, a right ventricle 11c, and a right atrium 11d). The four-chamber cross-sectional image is known to be a cross section including a mitral valve A and a cardiac apex C which are characteristic portions of the heart. Reference symbol B represents a portion referred to as a "left ventricle center" and is positioned at a middle point between the mitral valve A and the cardiac apex C. A vector directed from the left ventricle center B to the cardiac apex C is referred to as a long axis Y. A vector orthogonal to the long axis Y on the four-chamber cross-sectional image is referred to as a short axis X.

Subsequently, a three-dimensional image coordinate system of the three-dimensional image data (coordinate system of three-dimensional image space) will be described with reference to FIG. 3.

As shown in FIG. 3(a), a three-dimensional image space 20 included in the image data in the three-dimensional image coordinate system is expressed by three coordinate axes x, y, and z. The X-axis represents a vector from the left to the right of a body, the Y-axis has a vector from the anterior part to the posterior part of the body, and the Z-axis has a vector in the direction of the body axis toward the feet.

As shown in FIGS. 3(b) to (d), respective cross-sectional images 21a, 21b, 21c in the three-dimensional image space 20 are images obtained by taking the image data apart along planes 20a, 20b, 20c in parallel to the coordinate axes. The respective cross sections 20a, 20b, 20c are referred to as an "Axial cross section", a "Sagittal cross section", and a "Coronal cross section", and the respective cross-sectional images 21a, 21b, 21c are referred to as an "Axial cross-sectional image", a "Sagittal cross-sectional image", and a "Coronal cross-sectional image", respectively.

Figure 4:
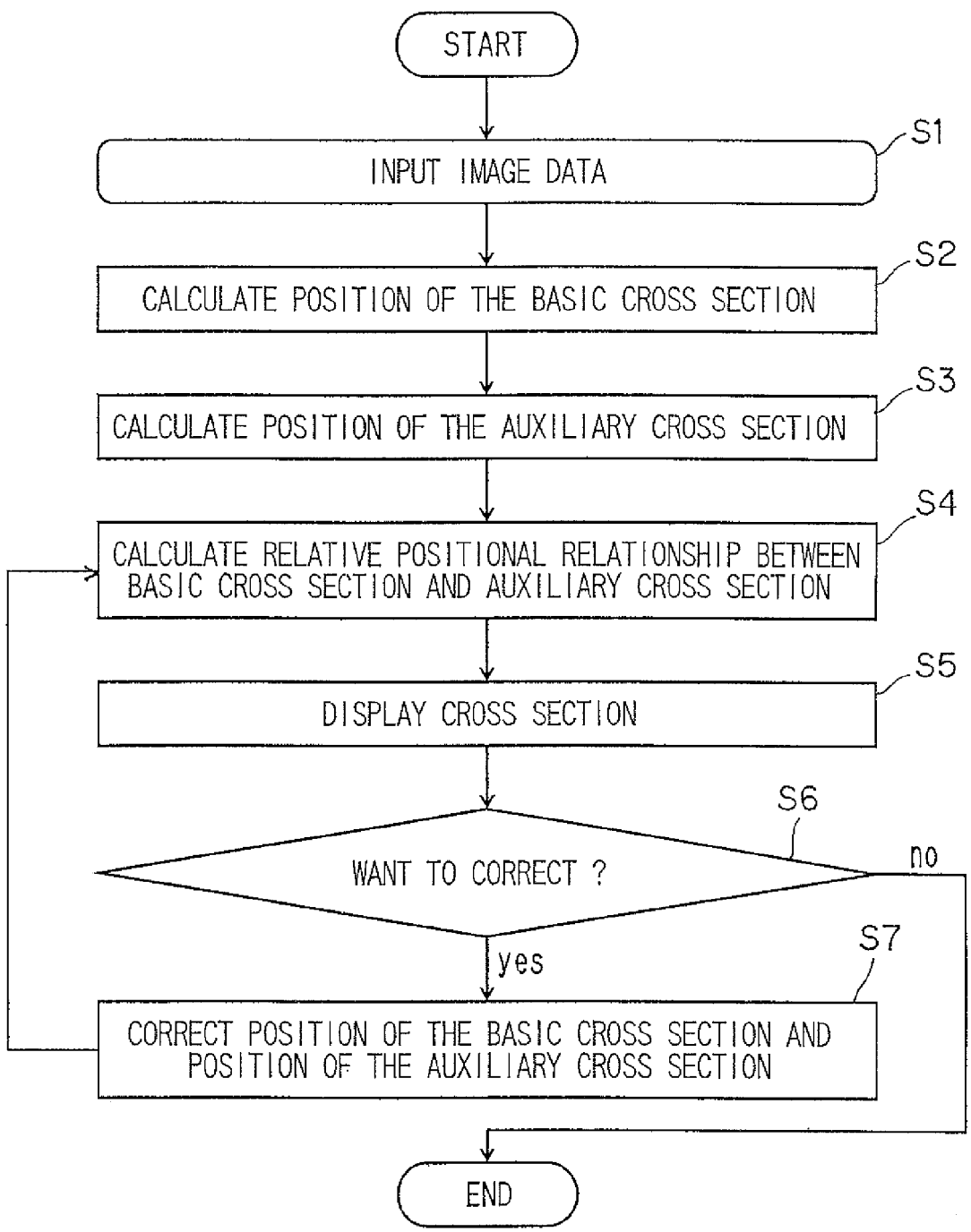
FIG. 4 is a flowchart of the image processing apparatus.

Referring now to FIG. 4, an action of the medical-use image processing apparatus 1 will be described. FIG. 4 is a flowchart showing an action of the medical-use image processing apparatus.

In Step S1, the image processing apparatus outputs a image data as a three-dimensional volume data to the basic position calculating unit 2. The image data may be entered directly from various types of imaging apparatus or an image data stored in an image server or the like may be entered.

In Step S2, the basic position calculating unit 2 calculates the position of the basic cross section from the image data. The generating unit 4 generates the basic cross-sectional image from the position of the basic cross-section and the image data.

The "calculation of the position of the basic cross section" means to set the basic cross section in the three-dimensional image space 20 of the three-dimensional volume data, such that an arbitrary portion used for diagnosis is included on an image of the basic cross section (hereinafter, referred to as "basic cross-sectional image"). Also, the "position of the basic cross section" means a spatial position of the basic cross section in the three-dimensional image space 20, and is expressed by position parameters which allow the basic cross-sectional image to be obtained uniquely from the three-dimensional volume data. For example, the position parameters, includes a center coordinate point o of the basic cross section on the three-dimensional image space 20 defined by an expression (1), and orthogonal two vectors u, v on the basic cross section defined by an expression (2).

$$O=(O_x, O_y, O_z) \quad (1)$$

$$u=(u_x, u_y, u_z), v32\ (v_x, v_y, v_z) \quad (2)$$

The two vectors u, v are capable of defining the basic cross-sectional image uniquely as long as they do not extend in parallel. However, for the sake of convenience of description in the embodiment, these two vectors u, v are described as extending orthogonally to each other. In other words, the calculation of the position of the basic cross section is equivalent to obtain the position parameters o, u, v.

The calculation of the position of the basic cross section may be calculated, manually as shown in Patent Document 1, for example, or may be calculated automatically using a method disclosed in JP-A-2002-140689.

When the position of the basic cross section is calculated, the generating unit 4 generates the basic cross-sectional image from the position of the basic cross section and the image data.

Figure 5A:
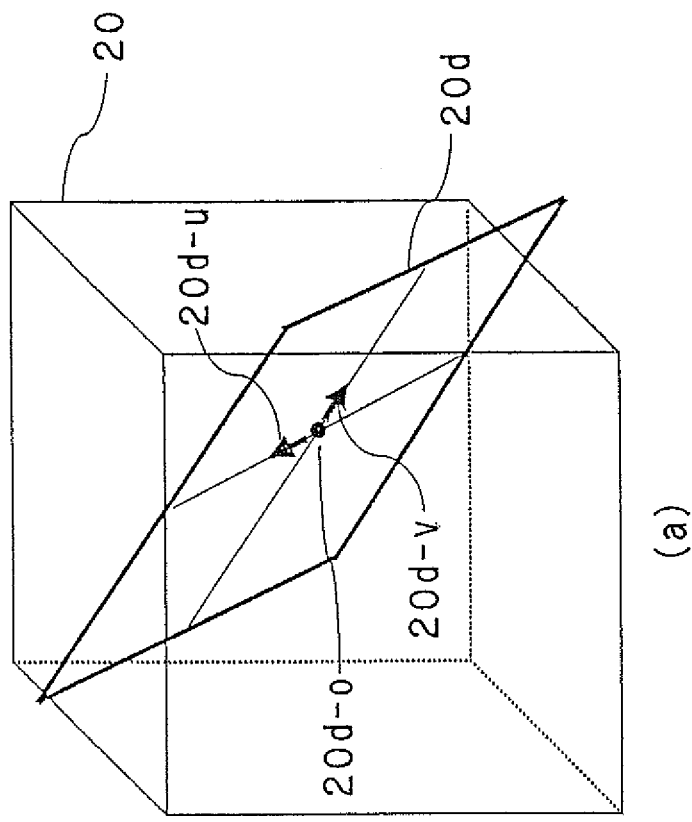
FIG. 5(a) is an explanatory drawing showing a position of a basic cross section of the three-dimensional image space 20, and (b) is a drawing showing a basic cross-sectional image.
Figure 5B:
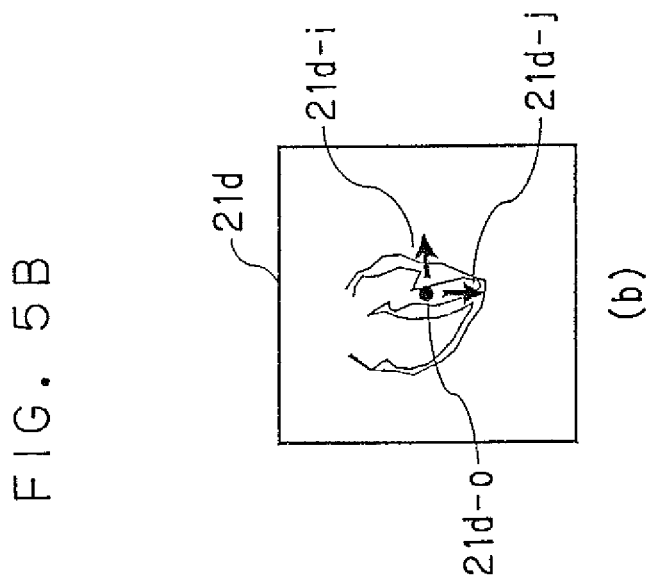
Figure 6A:
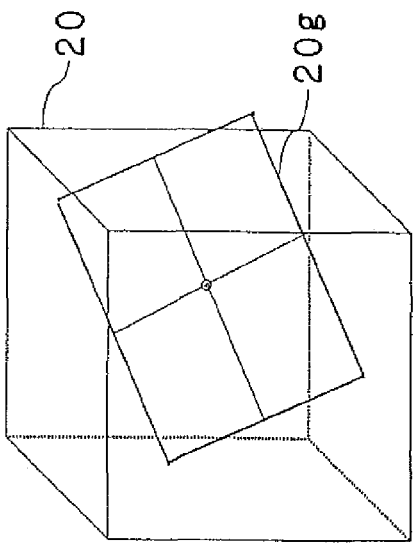
FIGS. 6(a) to (c) are explanatory drawings of a position of an auxiliary cross section of the three-dimensional image space 20, and (d) to (f) are drawings of an auxiliary cross-sectional image.
Figure 6B:
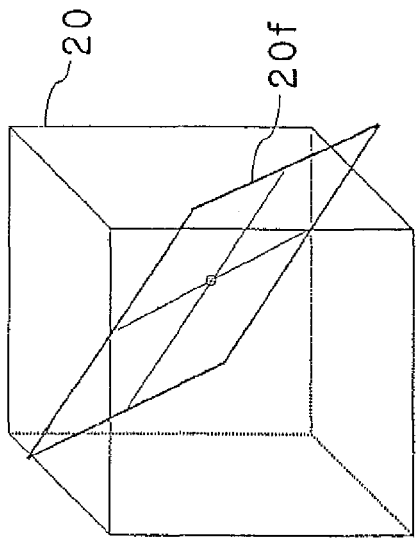
Figure 6C:
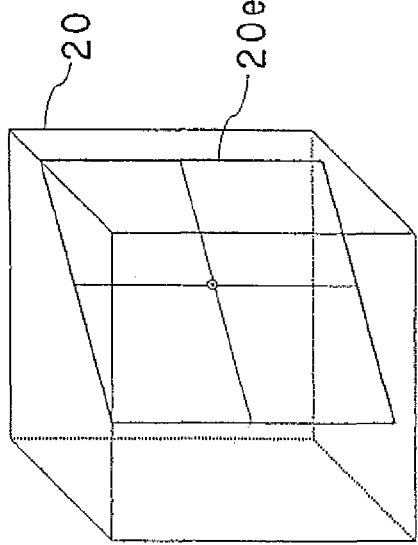
Figure 6D:
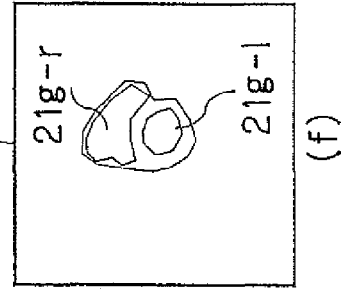
Figure 6E:
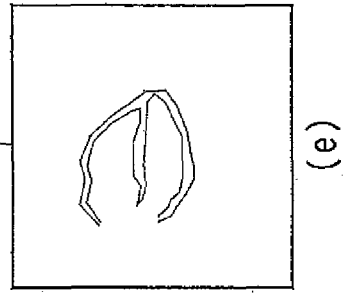
Figure 6F:
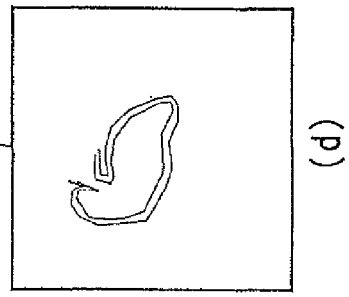

FIG. 5(a) shows how a basic cross section 20d is arranged in the three-dimensional image space 20 in a perspective view, and FIG. 5(b) shows an example of a generated basic cross-sectional image 1d. As shown in FIG. 5(a), the position of the basic cross section is expressed, for example, a center coordinate point $o_{20d}$ of the basic cross section 20d in the three-dimensional image space 20 and two vectors $u_{20d}$, $v_{20d}$ parallel to the basic cross section 20d and orthogonal to each other. The center coordinate point $o_{21d}$ in FIG. 5(a) corresponds to an image center point $o_{21d}$ in FIG. 5(b), the vector $u_{20d}$ in FIG. 5(a) corresponds to a horizontal vector $i_{21d}$ on the basic cross-sectional image 21d in FIG. 5(b), and the vector $v_{20d}$ in FIG. 5(a) corresponds to a vertical vector $j_{21d}$ of the basic cross-sectional image 21d in FIG. 5(b). In the drawing, since the subscripts are too small to read if written as "$u_{20d}$", it is expressed as "20d-u". Other vectors are also in the same manner in the drawings.

In Step S3, the auxiliary position calculating unit 3 calculates the position of the auxiliary cross-section on the basis of the position of the basic cross section. The generating unit 4 generates the auxiliary cross-sectional image from the position of the calculated auxiliary cross section and the image data.

The "auxiliary cross section" is a cross section obtained supplementarily to make it easier for the user to verify the position of the basic cross section, and is a cross section intersecting the basic cross section. For example, as the auxiliary cross section, an Axial cross section or a Sagittal cross section which is a cross section intersecting the basic cross section and includes an arbitrary portion used for diagnosis are used. Also, by employing the cross section calculated relatively from the position of the basic cross section as the auxiliary cross section, the position of the basic cross section can be verified further effectively.

A method of calculating auxiliary cross sections $20e$, $20f$, $20g$ relatively from the basic cross section $20d$ will be described with reference to FIG. 6.

The center coordinate point $o_{20d}$ of the basic cross section $20d$ is set as an expression (3).

$$o_{20d} = (o_{20d\_x}, o_{20d\_y}, o_{20d\_z}) \quad (3)$$

The orthogonal two vectors $u_{20d}$, $v_{20d}$ are set as an expression (4).

$$u_{20d} = (u_{20d\_x}, u_{20d\_y}, u_{20d\_z}), v_{20d} = (v_{20d\_x}, v_{20d\_y}, v_{20d\_z}) \quad (4)$$

At this time, as shown in FIG. 6($a$), the first auxiliary cross-section $20e$ is a plane parallel to the Z-axis and the long axis Y of the three-dimensional image space $20$. Orthogonal two vectors $u_{20e}$, $v_{20e}$ may be expressed as an expression (5).

$$u_{20e} = (u_{20d\_x}, u_{20d\_y}, 0), v_{20e} = (0,0,1) \quad (5)$$

As shown in FIG. 6($b$), the second auxiliary cross section $20f$ is a plane parallel to a normal vector of the first auxiliary cross section $20e$ and the long axis Y. Orthogonal two vectors $u_{20f}$, $v_{20f}$ may be expressed as an expression (6).

$$u_{20f} = u_{20d}, v_{20f} = u_{20e} \times v_{20e} \quad (6)$$

For reference sake, the sign "×" means vector product calculation.

As shown in FIG. 6($c$), the third auxiliary cross section $20g$ is a plane including the normal vector of the first auxiliary cross section $20e$ and a normal vector of the second auxiliary cross section $20f$. Orthogonal two vectors $u_{20g}$, $v_{20g}$ may be expressed as an expression (7).

$$u_{20g} = u_{20f} \times v_{20f}, v_{20g} = v_{20f} \quad (7)$$

Center coordinate points $o_{20e}$, $o_{20f}$, $o_{20g}$ of the respective auxiliary cross sections $20e$, $20f$, $20g$ use the center coordinate point of the basic cross section $20d$, for example, as shown in an expression (8).

$$o_{20e} = o_{20f} = o_{20g} = o_{20d} \quad (8)$$

In this manner, the respective auxiliary cross sections $20e$, $20f$, $20g$ may be calculated relatively from the basic cross section $20d$.

The generating unit 4 generates auxiliary cross-sectional images $21e$, $21f$, $21g$ from the respective positions of the auxiliary cross section as shown in FIGS. 6($d$) to ($f$). When the basic cross-sectional image $21d$ of the basic cross section $20d$ is the four-chamber cross-sectional image, the auxiliary cross sectional images $21e$, $21f$, $21g$ generated from the auxiliary cross sections $20e$, $20f$, $20g$ are referred to as the "two-chamber cross-sectional image", a "horizontal cross-sectional image", and the "left-chamber short axis image", respectively. However, the auxiliary cross section is not limited thereto, and may be obtained with reference to a body axis of a person to be diagnosed.

In this manner, by calculating relatively from the position of the basic cross section, the auxiliary cross section which includes the characteristic portion of the heart may easily be set, so that the auxiliary cross-sectional image which allows easy verification of the basic cross section may be generated.

In Step S4, the relationship calculating unit 5 calculates the information on relative positional relationship of the basic cross section $20d$ and the auxiliary cross sections $20e$, $20f$, $20g$.

Here, the term "information on positional relationship" means, for example, a segment at the intersection between the basic cross section and the auxiliary cross section, and spatial coordinate points of the characteristic portions included commonly in the basic cross-sectional image and the auxiliary cross-sectional image.

An example of calculation of the information on the positional relationship will be described with reference to FIGS. 7($a$) to ($d$).

Since the basic cross section $20d$ and the second and third auxiliary cross-sectional images $21e$, $21f$ are planes including the long axis Y and intersecting with each other as shown in FIGS. 7($a$), ($b$), ($d$), the relationship calculating unit 5 calculates segments $v_{21d}$, $v_{21e}$, $v_{21f}$ indicating the long axis Y (that is, the vertical direction on the basic cross-sectional image $21d$). Also, when the basic position calculating unit 2 calculates the positions of the mitral valve A, the left ventricle center B, and the cardiac apex C, namely, of the characteristic portions relating to the heart, the relationship calculating unit 5 calculates the positions of the respective portions on the respective cross sections as indicated by coordinate points $p_{21d}$, $p_{21e}$, $p_{21f}$ indicated by stars, squares and triangles in FIGS. 7($a$), ($b$), ($c$). Since the third auxiliary cross section $20g$ is a plane orthogonal to the long axis Y as shown in FIG. 7($c$), the relationship calculating unit 5 calculates the direction of the short axis X on the third auxiliary cross-sectional image $21g$ as indicated by a coordinate point $p_{21g}$, and a segment $v_{21g}$.

In this manner, by calculating the common segment included in plural cross sections or coordinate points of the portions, the information on the positional relationship relative to the basic cross section may be obtained.

In Step S5, the combining unit 6 combines the generated basic cross-sectional image $21d$ and the auxiliary cross-sectional images $21e$, $21f$, $21g$, and the segment and the coordinate points as the information on the positional relationship and displays the same on the display unit 9.

For example, the combining unit 9 overlaps the information on the positional relationship with the Axial cross-sectional image $20a$, the Sagittal cross-sectional image $21b$, the Coronal cross-sectional image $21c$, the basic cross-sectional image $21d$, and the auxiliary cross-sectional images $21e$, $21f$, $21g$ or displays the information on the positional relationships of the respective cross sections in the three-dimensional image space $20$ on the display unit 9.

In Step S6, when the user operates the input unit 7 and corrects the information on the positional relationship, and the correcting unit 8 receives the correction of the information on the positional relationship, the procedure goes to Step S7 (in the case of "Yes" in FIG. 4), and if the user does not make any correction, the procedure ends (in the case of "no" in FIG. 4).

In Step S7, the correcting unit 8 corrects the position of the basic cross section and the position of the auxiliary cross section on the basis of the accepted information on the correction of the information on the positional relationship. Then, the procedure goes back to Step S4, and the relationship calculating unit 5 calculates the information of the relative positional relationship between the basic cross section 20d and the auxiliary cross sections 20e, 20f, 20g again.

The correction will be described with reference to FIG. 8.

First of all, the combining unit 6 combines the information on the positional relationship calculated by the relationship calculating unit 5 with the basic cross section 20d in the three-dimensional image space 20 shown in FIG. 8(a), the Axial cross-sectional image 21a, the Coronal cross-sectional image 21b, and the Sagittal cross-sectional image 21c of the image data shown in FIGS. 8(b) to (d), the auxiliary cross-sectional images 21e, 21f, 21g shown in FIGS. 8(e) to (g), and the basic cross-sectional image 21d shown in FIG. 8(i) and displays the same on the display unit 9. The user, having medical knowledge that the long axis Y passes the center of the left venticle, is capable of verifying easily that the left side of the long axis Y is needed to be corrected upward from the first auxiliary cross-sectional image 21e, and that the left side of the long axis Y is needed to be corrected downward from the second auxiliary cross-sectional image 21f by viewing the display unit 9. Also, the user has medical knowledge that the third auxiliary cross-sectional image 21g is an example of the left-chamber short axis view, and the short axis X passes the center of a left venticle $l_{21g}$ and the left corner of a right venticle $r_{21g}$, the direction to be corrected may be verified easily from the third auxiliary cross-sectional image 21g.

Subsequently, the user corrects the information on the positional relationship via the mouse of the input unit 7 as the user interface. For example, the user operates the input unit 7 to point out the segments or the coordinate points as the information on the positional relationship between the basic cross section and the auxiliary cross section with a pointer 30, and moves the segments or the coordinate points upward, downward, leftward and rightward on the screen for each of the cross-sectional images. The correcting unit 8 accepts the information of movement as the correction information. In other words, the "correction information" is a two-dimensional vector including the direction of movement and the length of movement of the segments and the coordinate points, which are information on the positional relationship for each of the cross-sectional images.

Subsequently, the correcting unit 8 converts the direction of movement and the length of the movement on the two-dimensional cross-sectional image using each of the correction information in the two-dimensional vector of the respective cross-sectional images into the corrected vector in the three-dimensional image space 20. Then, the position of the basic cross section is corrected on the basis of the converted three-dimensional corrected vector. The correcting unit 8 corrects the position parameters o, u, v of the position of the basic cross section into position parameters o', u', v' shown in an expression (9) shown below.

$$o'_{20d} = (o'_{20d\_x}, o'_{20d\_y}, o'_{20d\_z}), u'_{20d} = (u'_{20d\_x}, u'_{20d\_y}, u'_{20d\_z}), v'_{20d} = (v'_{20d\_x}, v'_{20d\_y}, v'_{20d\_z}) \quad (9)$$

Also, the correcting unit 8 corrects the position parameter of the position of the auxiliary cross section by calculating the expression (5) to the expression (9) using the positional parameters o', u' v' of the corrected position of the basic cross section.

The generating unit 4 generates a basic cross-sectional image corrected from the corrected position of the basic cross section and an auxiliary cross-sectional image corrected from the corrected position of the auxiliary cross section.

The relationship calculating unit 5 recalculates the information on the positional relationship between the basic cross section and the auxiliary cross section on the basis of the position parameter of the corrected position of the basic cross section and the position parameter of the corrected position of the auxiliary cross section.

The combining unit 6 combines the corrected basic cross-sectional image 21d and the auxiliary cross-sectional images 21e, 21f, 21g, and the segments and the coordinate points as the information on the positional relationship corrected by the correction information and displays the same on the display unit 9.

Accordingly, the user is capable of diagnosing using the basic cross-sectional image 20d or the auxiliary cross-sectional images 21e, 21f, 21g corrected by the input unit 7.

According to the present embodiment, by displaying the information of relative positional relationship of the respective cross sections overlapped with the basic cross-sectional image and the auxiliary cross-sectional image, the spatial position on the basic cross section required for the diagnosis can be verified easily.

Also, by correcting the information on the positional relationship from the basic cross-sectional image and the auxiliary cross-sectional image, the position of the basic cross section can be corrected easily.

The preset invention is not limited to the embodiment described above and may be implemented by modifying variously without departing the scope of the invention.

For example, the positional parameters representing the cross-sectional position are expressed by the center point of the cross section on the three-dimensional image space 20 and the two orthogonal vectors u, v on the cross section. However, the invention is not limited thereto, and may be any parameters which can define the spatial position of the cross section uniquely. For example, it may be represented by an initial point of the cross section on the three-dimensional image space 20, and two orthogonal vectors u, v on the cross section from this initial point. Also, it may be represented by three vectors on the cross section. Also, it may be represented by coordinate points at four apexes of a rectangular shape representing the cross section in the three-dimensional image space 20.

In the embodiment described above, the portion to be diagnosed is the heart. However, portions other than the heart may be intended. Also, plural portions may be intended for diagnosis simultaneously.

Also, in the embodiment described above, the image showing how the basic cross section 20d is arranged in the three-dimensional image space 20 as shown in FIG. 8(a) in a perspective view is also displayed on the display unit 9. However, this image does not necessarily have to be displayed, and the spatial position of the basic cross section required for the diagnosis can be verified easily by displaying the basic cross-sectional image 21d and other auxiliary cross-sectional images 21 shown in FIGS. 8(b) to (i).

The invention claimed is:

1. An image processing apparatus for diagnostic imaging, comprising:
   a microprocessor configured to:
      estimate, from a three-dimensional image data of an object including an arbitrary portion, a position of plural characteristic portions of the arbitrary portion, and to calculate a position of a first cross section to include the plural characteristic portions of the arbitrary portion, a position of a second cross section intersecting the position of the first cross section and the second cross section including the plural characteristic portions of the arbitrary portion, and information on a positional relationship of the position of the plural characteristic portions and a line passing through the positions of the plural characteristic portions indicating the relative positional relationship between the position of the first cross section and the position of the second cross section;

generate a first cross-sectional image using the three-dimensional image data and the position of the first cross section and generate a second cross-sectional image using the three-dimensional image data and the position of the second cross section;

combine the information on the positional relationship with at least one of the first cross-sectional image and the second cross-sectional image and generate a combined image to be displayed on a display.

2. The apparatus according to claim 1, comprising:
an interface which allows a user to enter information; and
the microprocessor further configured to correct the position of the first cross section and the position of the second cross section when correction information relating to the information on the positional relationship is entered from the input unit,
wherein
the microprocessor calculates the information on the positional relationship indicating the relative positional relationship between the corrected position of the first cross section and the corrected position of the second cross section, and
the microprocessor combines the information on the positional relationship on the basis of the entered correction information with the corrected first cross-sectional image and the corrected second cross-sectional image, respectively.

3. The apparatus according to claim 2,
wherein the position of the second cross section is calculated on the basis of the position of the first cross section.

4. The apparatus according to claim 2,
wherein the position of the second cross section is calculated on the basis of a body axis and the image data.

5. The apparatus according to claim 1,
wherein the position of the first cross section and the position of the second cross section are represented by a coordinate point and two vectors from the coordinate point in a three-dimensional image space, three vectors in the three-dimensional image space, or coordinate points at four apexes of the first cross section and the second cross section.

6. A method of processing an image for diagnostic imaging, comprising:
a step for determining, from a three-dimensional image data of an object including an arbitrary portion, a position of plural characteristic portions of the arbitrary position, and to calculate a position of a first cross section to include the plural characteristic portions of the arbitrary portion, a position of a second cross section intersecting the position of the first cross section and the second cross section including the plural characteristic portions of the arbitrary portion, and information on a positional relationship of the position of the plural characteristic portions and a line passing through the positions of the plural characteristic portions indicating the relative positional relationship between the position of the first cross section and the position of the second cross section;

a step for generating a first cross-sectional image using the three-dimensional image data and the position of the first cross section and generating a second cross-sectional image using the three-dimensional image data and the position of the second cross section;

a step for combining the information on the positional relationship with at least one of the first cross-sectional image and the second cross-sectional image and generating a combined image to be displayed on a display.

7. The apparatus according to claim 1,
wherein the arbitrary portion is a heart.

8. The apparatus according to claim 2,
wherein the plural characteristic portions include a mitral valve and a cardiac apex.

9. The apparatus according to claim 2,
wherein the first cross-sectional image and the second cross-sectional image are each any one of a four-chamber cross-sectional image, a two-chamber cross-sectional image, a horizontal cross-sectional image, and a left-chamber short axis image.

10. The apparatus according to claim 1,
wherein the information on the positional relationship is a segment at an intersection between the first cross-sectional image and the second cross-sectional image.

11. The apparatus according to claim 1,
wherein the information on the positional relationship is coordinate points of the characteristic portions included commonly in the first cross-sectional image and the second cross-sectional image.

12. The apparatus according to claim 1,
wherein the position of the second cross section is determined so that the second cross section further includes at least one characteristic portion which is not included in the first cross section.

13. The apparatus according to claim 1, further comprising a display to display the combined image.

* * * * *